United States Patent
Morrow et al.

(10) Patent No.: US 6,850,847 B2
(45) Date of Patent: Feb. 1, 2005

(54) DEVICE FOR DETERMINING THERMOPHYSICAL PROPERTIES OF A MULTI-COMPONENT GAS AT ARBITRARY TEMPERATURE AND PRESSURE

(75) Inventors: Thomas B. Morrow, San Antonio, TX (US); Kendricks A. Behring, II, Gilbert, AZ (US)

(73) Assignee: Southwest Research Institute, San Antonio, TX (US)

( * ) Notice: Subject to any disclaimer, the term of this patent is extended or adjusted under 35 U.S.C. 154(b) by 0 days.

(21) Appl. No.: 10/770,768

(22) Filed: Feb. 3, 2004

(65) Prior Publication Data

US 2004/0158411 A1 Aug. 12, 2004

Related U.S. Application Data

(63) Continuation of application No. 10/237,492, filed on Sep. 9, 2002, now Pat. No. 6,704,660, which is a continuation-in-part of application No. 09/550,431, filed on Apr. 17, 2000, now Pat. No. 6,604,051.

(51) Int. Cl.[7] .................................................. G01N 9/00
(52) U.S. Cl. ............................ 702/27; 702/23; 702/24
(58) Field of Search ............................. 702/23, 24, 27, 702/30, 137, 142; 73/24.05, 25.01, 61, 596, 600, 861.61

(56) References Cited

U.S. PATENT DOCUMENTS

| | | | |
|---|---|---|---|
| 4,489,592 A | 12/1984 | Pacanowski et al. | 73/24.05 |
| 4,596,133 A | 6/1986 | Smalling et al. | 73/24 |
| 5,285,675 A | 2/1994 | Colgate et al. | 73/23.2 |
| 5,311,447 A | 5/1994 | Ulrich | 702/50 |
| 5,486,107 A | 1/1996 | Bonne | 431/12 |
| 5,537,854 A | 7/1996 | Phillips et al. | 73/24.01 |
| 5,932,793 A | 8/1999 | Dayton et al. | 73/24.05 |
| 6,047,589 A | 4/2000 | Hammond et al. | 73/24.01 |
| 6,065,328 A | 5/2000 | Dayton et al. | 73/25.01 |
| 6,076,392 A | 6/2000 | Drzewiecki | 73/23.2 |
| 6,209,387 B1 | 4/2001 | Savidge | 73/24.05 |
| 6,286,360 B1 | 9/2001 | Drzewiecki | 73/24.01 |
| 6,604,051 B1 * | 8/2003 | Morrow et al. | 702/24 |
| 6,704,660 B2 * | 3/2004 | Morrow et al. | 702/24 |

FOREIGN PATENT DOCUMENTS

| | | | |
|---|---|---|---|
| DE | 198 23 193 A1 | 11/1999 | G01N/9/00 |
| EP | 1 063 525 A2 | 7/1999 | G01N/33/22 |
| EP | 0 939 317 A2 | 9/1999 | G01N/33/22 |
| EP | 0 959 354 A2 | 11/1999 | G01N/33/22 |
| WO | 93/08457 | 4/1993 | G01N/9/00 |
| WO | 99/10740 | 3/1999 | G01N/33/22 |

OTHER PUBLICATIONS

International Preliminary Examination Report PCT/US01/12217, Jul. 8, 2002.

(List continued on next page.)

*Primary Examiner*—Bryan Bui
(74) *Attorney, Agent, or Firm*—Baker Botts L.L.P.

(57) ABSTRACT

A computer product for determining thermodynamic properties of a natural gas hydrocarbon, when the speed of sound in the gas is known at an arbitrary temperature and pressure. Thus, the known parameters are the sound speed, temperature, pressure, and concentrations of any dilute components of the gas. The method uses a set of reference gases and their calculated density and speed of sound values to estimate the density of the subject gas. Additional calculations can be made to estimate the molecular weight of the subject gas, which can then be used as the basis for mass flow calculations, to determine the speed of sound at standard pressure and temperature, and to determine various thermophysical characteristics of the gas.

17 Claims, 3 Drawing Sheets

OTHER PUBLICATIONS

International Search Report PCT/US 01/12217, Nov. 13, 2001.

Wild, K.R., "Controlling Processes that are Sensitive to Natural Gas Quality", presented at the 21st World Gas Conference, Nice France, Jun. 6–9, 2000.

U.S. Pending Continuation–in–Part patent application Ser. No. 10/401,206 entitled "Indirect Measurement of Nitrogen in a Multi–Component Gas by Measuring the Speed of Sound at Two States of the Gas", filed by Thomas B. Morrow et al, Filed Mar. 27, 2003.

U.S. Pending Continuation–in–Part patent application Ser. No. 10/460,579 entitled "Indirect Measurement of Nitrogen in a Multi–Component Natural Gas by Heating the Gas", filed by Thomas B. Morrow et al., Filed Jun. 12, 2003.

* cited by examiner

DEVICE FOR DETERMINING THERMOPHYSICAL PROPERTIES OF A MULTI-COMPONENT GAS AT ARBITRARY TEMPERATURE AND PRESSURE

RELATED APPLICATION

This application is a continuation of U.S. application Ser. No. 10/237,492 filed Sep. 9, 2002, now U.S. Pat. No. 6,704,660, entitled "A System and Method to Determine Thermophysical Properties of a Multi-Component Gas at Arbitrary Temperature and Pressure", which is continuation-in-part application of U.S. application Ser. No. 09/550,431 filed Apr. 17, 2000, entitled, "System and Method to Determine Thermophysical Properties of a Multi-Component Gas", now U.S. Pat. No. 6,604,051.

GOVERNMENT LICENSE RIGHTS

The U.S. Government has a paid-up license in this invention and the right in certain circumstances to require the patent owner to license others on reasonable terms as provided for by the terms of Contract No. DE-FC21-96MC33033 for the U.S. Department of Energy.

TECHNICAL FIELD OF THE INVENTION

This invention relates to the field of measuring thermophysical properties of gases, and more particularly, to the determination of thermophysical gas properties using gross inferential properties and empirical correlations, at arbitrary temperature and pressure.

BACKGROUND OF THE INVENTION

Virtually all natural gas produced in the U.S. is used as fuel. As such, its intrinsic value lies in its heating value. However, because of the lack of low-cost, reliable instrumentation for measuring energy content or energy flow rate, natural gas traditionally has been bought, sold, and transported on the basis of volume. Gas composition and energy content are currently determined by periodically analyzing sampled gas from the pipeline.

With the advent of deregulation and open access in the gas pipeline industry, large-volume, long-term commodity gas contracts gave way to more small-volume, short-term transportation contracts, taking gas "packages" from many supply and storage fields with widely varying gas qualities. These gas packages lose their identity when mixed in the pipeline, and the purchaser receives whatever is in the pipeline at the time of need.

Without economical means for continuously (real-time or near real-time) measuring the quality of gas entering and exiting the pipeline, neither the supplier nor the end-user can assure quality of the commodity exchange. Also, gas supplies cannot be blended to assure conformity to a quality standard. End-users withdraw gas on the basis of energy needs. If the energy content is low, end-users simply withdraw (and pay for) more gas than anticipated.

Current technology provides two approaches to energy flow rate measurement for natural gas. The first requires a composition assay and a flow rate measurement. The composition assay allows calculating the heating value of the gas, and is also required to calculate selected gas properties (e.g., gas density) needed to determine energy flow rates. The second approach measures gas density and heating value directly, using special instrumentation, and requires no composition assay.

SUMMARY OF THE INVENTION

The system and method of the present invention provide for determination of thermophysical properties of a multi-component hydrocarbon gas. Exploiting the interdependence of properties the components of such a gas allows characterizing its hydrocarbon energy without a detailed composition assay.

The method described herein involves determining the diluent concentrations (e.g., predominantly nitrogen and carbon dioxide) of these gas. These concentrations may be measured or inferred from other measurements with approximate accuracy, as they account for only a small fraction of the whole natural gas mixture. The remaining hydrocarbon gas components (i.e., the majority of the gas mixture) can be characterized by inferential properties, without differentiation of species. For the purpose of the present invention, three inferential properties were selected in an exemplary fashion. These are the speed of sound, carbon dioxide concentration, and nitrogen concentration. The speed of sound may be measured at any arbitrary temperature and pressure.

As a specific example, the concentration of carbon dioxide and nitrogen are determined, along with the speed of sound in the gas, to determine a thermophysical property (e.g. the Mixture Molar Ideal Gross Heating Value). An empirical correlation exists between the thermophysical property, the speed of sound, the concentration of carbon dioxide, and the concentration of nitrogen in the gas.

Depending on the gas components for which the concentration is determined, various thermophysical properties can be determined more or less accurately. For example, the Mixture Molar Ideal Gross Heating Value, the Mixture Molecular Weight, the Mass-Based Heating Value, and the Density of the gas can all be determined within about ±0.02% of selected model values by implementing the system and method of the present invention.

The concentration of the diluent gas components may be determined directly (e.g., via measurement), or indirectly. For example, the concentration of a particular gas component may be determined by correlating a thermodynamic property for the selected component with one or more directly measurable inferential properties of the component.

DETAILED DESCRIPTION OF THE INVENTION

System Overview

Figure 1:
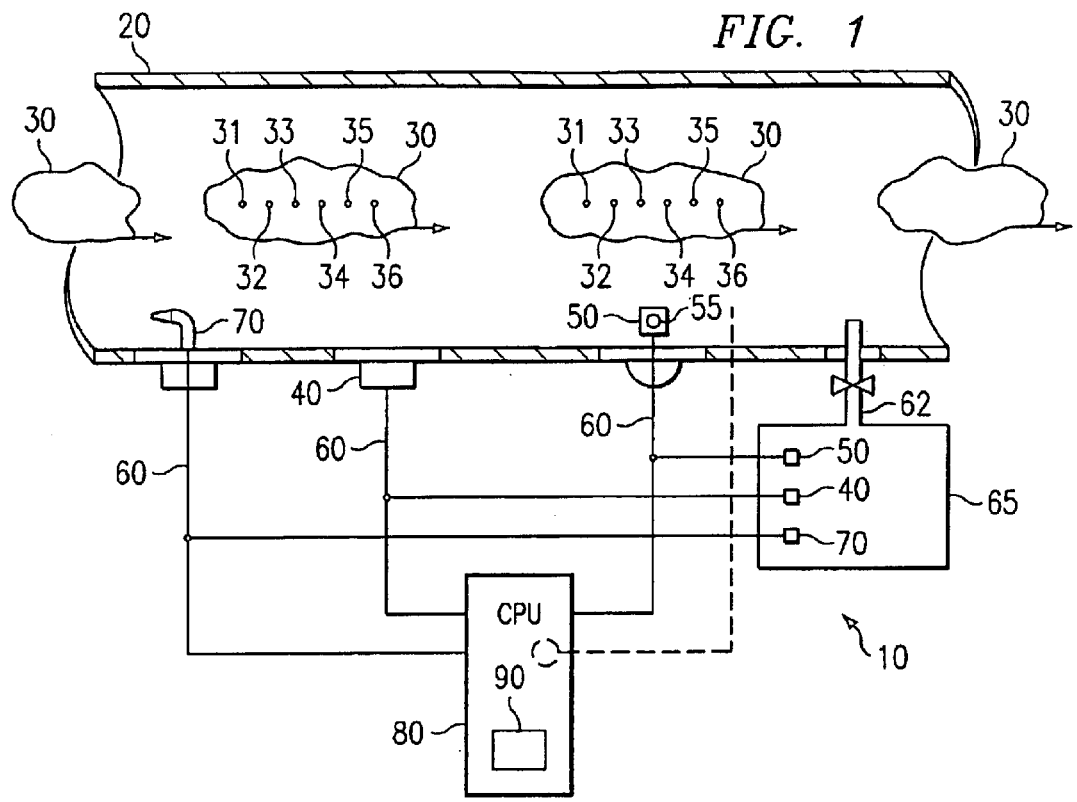
FIG. 1 is a block diagram of the apparatus of the present invention.

FIG. 1 illustrates the apparatus of the present invention. The system 10 for determining thermophysical properties of a gas is typically installed on a gas pipeline. The pipe 20 is shown in a cut-away view carrying a multi-component gas 30 (or, using alternative terminology, a gas having a plurality of components 30). Typically, such components include nitrogen 31, carbon dioxide 32, methane 33, ethane 34, propane 35, and heavier hydrocarbons 36, each component existing within the gas 30 in varying proportions.

System 10 includes a sound velocity measurement device 40 adapted to measure the speed of sound in the gas 30. This device is preferably an inexpensive ultrasonic flow meter, such as those produced by Siemens for residential applications in the European gas market, e.g. the Siemens E6 domestic gas meter. In addition, any of the following meters are suitable for use as a sound velocity measurement device 40 in the gas 30: Daniel Senior Sonic, Junior Sonic, and UltraTap ultrasonic flow meters; the Smith Meter Kongsberg MPU1200 ultrasonic flow meter; the Panametrics Ultrasonic Transit-Time flow meter; and the Instromet Q Sonic-2S, -3S, and -5S ultrasonic flow meters. The sound velocity measurement device 40 may also comprise an array of ultrasonic sensors and associated electronics configured specifically to measure the speed of sound, as is well known in the art.

Also comprising an element of system 10 is a concentration measurement device 50 adapted to determine the concentration of a plurality of components comprising the gas 30. The concentration measurement device 50 can include a commercial, non-dispersive infrared sensor, which may be similar to or identical to the Vaisala model GMM11, which measures the concentration of carbon dioxide using infrared energy absorption. Other suitable instruments which may comprise the device 50 and which can be used to determine component concentrations include sensors or meters to directly measure the concentration of nitrogen, carbon dioxide, and/or other components.

As an alternative approach, the concentration measurement device 50 may be used to determine a gas concentration inferentially, in combination with measurements of sound speed and another gas component concentration. Examples include the inferential determination of $N_2$ by any of the following methods: measuring the sound speed at two different pressures and temperatures, measuring heat dissipation and temperature rise in a container having a fixed volume, measuring heat dissipation and temperature rise in a gas stream flowing at a constant rate, or independently measuring the gas density.

The sound velocity measurement device 40 and the concentration measurement device 50 are typically connected so as to be in electrical communication with the processor 80 using cables 60. A correlation device 55 may also comprise a part of the concentration measurement device, or reside as an independent correlation device 55 outside the measurement device 50, such as in the processor 80. The correlation device 55 may be incorporated as a software module within the processor 80, or as a separate hardware module, such as a Digital Signal Processor (DSP) or some other computational device dedicated to effecting the correlation calculations described hereinafter. That is, the computational load on the processor 80 may be divided between the processor 80 and the correlation device 55. However, in certain applications, there is no need for this type of division, and the processor 80 may be suitable for gathering data from the various sensors and making the correlation computations necessary to carry out the method of the present invention. Typically, the processor 80 will have a memory 90 for storing the results of sensor measurements, programming information, and calculation results for chemical properties of the gas 30.

As can be seen in FIG. 1, the measurements of concentration and speed of sound can be made within the pipe 20 at flowing temperature and pressure. Alternatively, the measurements can be made within a gas sample, outside of the pipe, held in a sample chamber 65, for example. In this case, the gas may be sampled from within the pipe 20 by using a sample tube 62 which directs the gas sample into a sample chamber 65. Thus, any one or more of the measurements noted above can be made within the sample chamber 65 using the concentration measurement device 50, the sound velocity measurement device 40, and/or the natural gas flow meter 70. Measurements of any of these properties may be made within the pipe 20, within the sample chamber 65, or from a combination of the two locations. A preferred embodiment makes use of an existing ultrasonic flow meter 40 to measure the sound speed in the pipeline 20 at the flowing gas temperature and pressure, and a gas sample stream drawn off of the pipeline 20 through a sample tube 62 to measure the nitrogen and carbon dioxide concentrations.

Natural gas flow meters 70 may be generally classified as volume-based (ultrasonic, turbine, rotary, diaphragm, etc.), differential-based (orifice, annular, V-cone, etc.), and mass-based (Coriolis, thermal-mass, etc.). Any of these meters 70 may be used for energy measurement, but each meter classification requires the determination of different properties to complete the energy flow rate calculation. For example, volume-based meters require:

$$Q_{energy \atop volume-based} = Q_{v,std} H_{v,std} = \left(\frac{\rho Q_v}{\rho_{std}}\right)(\rho_{std} H_m) = Q_v(\rho H_m) = Q_v H_v \quad [1\text{-}1]$$

Flow Rates

To complete the energy flow rate calculation, volume-based meters require only the volume-based heating value, $H_v$ [Btu/acf], which is the product of flowing density, $\rho$[lbm/ft$^3$], and mass-based heating value, $H_m$ [Btu/lbm]. If traditional formulations of standard volumetric flow rate, $Q_{v,std}$[scf/h], and heating value, $H_{v,std}$[Btu/scf], are desired, then standard density, $\rho_{std}$ [typically measured in lbm/ft$^3$ at 60° F., 14.73 psia, at the flowing composition], is also needed.

Energy flow rate through a differential (pressure-based) meter requires:

$$Q_{energy, \atop differential-based} = Q_{v,std} H_{v,std} = \left(\frac{C\sqrt{\rho}}{\rho_{sd}}\right)(\rho_{std} H_m) = C(\sqrt{\rho} H_m) \quad [1\text{-}2]$$

Note that differential meters require determination of the flowing gas density, $\rho$[lbm/ft$^3$], and the mass-based heating value, $H_m$[Btu/lbm]. If traditional formulations of standard volumetric flow rate, $Q_{v,std}$[scf/h], and heating value, $H_{v,std}$ [Btu/scf], are desired, then standard density, $\rho_{std}$ [typically lbm/ft$^3$ at 60° F., 14.73 psia, at the flowing composition], is also needed. Note that the catch-all factor C depends on the viscosity, $\mu$ (through the discharge coefficient), and on the isentropic exponent, $\kappa$ (through the expansion factor), but these are of lesser importance.

Energy flow rate calculation using a mass-based meter requires:

$$Q_{energy, \atop mass-based} = Q_{v,std} H_{v,std} = \left(\frac{Q_m}{\rho_{std}}\right)(\rho_{std} H_m) = Q_m H_m \quad [1\text{-}3]$$

Only the addition of mass-based heating value, $H_m$ [Btu/lbm], is required to determine energy flow rate through a mass-based meter. If traditional formulations of standard volumetric flow rate, $Q_{v,std}$ [scf/h], and heating value, $H_{v,std}$ [Btu/scf], are desired, then the standard density, $\rho_{std}$, will also be needed to convert from a mass-basis to a standard-volume basis.

Equations [1—1] to [1-3] describe the property dependence of different meter classes with respect to energy measurement, but all properties are not equally difficult to determine. Chemical properties depend only on gas composition (chemical characterization). Thermodynamic properties depend on gas composition, temperature, and pressure. Furthermore, thermodynamic properties can become chemical properties (dependent only on gas composition) at a fixed temperature and pressure, although the chemical dependence will vary at different temperature and pressure conditions.

Thus, three natural gas properties are critical to energy measurement. Two chemical properties, $H_m$ and $\rho_{std}$, are required by all three meter classes, and an additional thermodynamic property ($\rho$) is required by volume-based and differential-based meters. Mass-based meters are uniquely independent of thermodynamic properties, an important advantage that makes flowing gas temperature and pressure irrelevant for this class of meters.

Other chemical properties, in addition to $H_m$ and $\rho_{std}$, are also useful. Mixture Molecular Weight, M [lbm/lb-mol], is useful as a data correlation intermediary to characterize gas composition, and may also be used to calculate Ideal Specific Gravity. Mixture Molar Ideal Gross Heating Value, $H_{n,ref}$ [kJ/mol, with chemical-enthalpies referenced to 25° C., 0.101325 MPa], is a useful intermediary to characterizing gas composition, especially gas density, $\rho$, from an existing equation of state.

The basis of inferential property determination is chemical characterization. Chemical properties are constant across gas-phase temperature and pressure conditions. In contrast, thermodynamic properties must be chemically characterized for selected temperature and pressure conditions.

Reference Gas Mixtures

For the purpose of defining various chemical properties and deriving data correlations, a database of 102 different natural gas compositions was developed. Of the first 51 compositions, 43 are unique. The remaining 51 compositions can be obtained by reversing the carbon dioxide and nitrogen concentrations of the first 51 compositions. The complete gas composition database is presented in Table 1.

TABLE I

| | nitrogen [mole %] | carbon dioxide [mole %] | methane [mole %] | ethane [mole %] | propane [mole %] | 1-butane [mole %] | n-butane [mole %] | 1-pentane [mole %] | n-pentane [mole %] | n-hexane [mole %] | n-heptane [mole %] | n-octane [mole %] |
|---|---|---|---|---|---|---|---|---|---|---|---|---|
| 1 | 0.4422 | 1.9285 | 84.3361 | 8.8946 | 3.1919 | 0.59064 | 0.39376 | 0.10950 | 0.07300 | 0.0325 | 0.0061 | 0.0012 |
| 2 | 1.6004 | 0.2331 | 95.5340 | 1.8790 | 0.4926 | 0.09066 | 0.06044 | 0.03522 | 0.02348 | 0.0309 | 0.0168 | 0.0034 |
| 3 | 5.6769 | 1.4546 | 85.1473 | 5.4174 | 1.5968 | 0.30438 | 0.20292 | 0.08694 | 0.05796 | 0.0391 | 0.0138 | 0.0019 |
| 4 | 0.6224 | 1.8643 | 85.4814 | 8.0607 | 2.8624 | 0.52170 | 0.34780 | 0.11346 | 0.07564 | 0.0398 | 0.0096 | 0.0008 |
| 5 | 5.4939 | 1.8292 | 84.3931 | 5.8857 | 1.6910 | 0.32742 | 0.21828 | 0.06942 | 0.04628 | 0.0296 | 0.0128 | 0.0033 |
| 6 | 5.3551 | 1.7802 | 84.4786 | 5.8782 | 1.7778 | 0.34002 | 0.22668 | 0.07050 | 0.04700 | 0.0309 | 0.0116 | 0.0034 |
| 7 | 1.6052 | 0.2339 | 95.5192 | 1.8835 | 0.4933 | 0.09108 | 0.06072 | 0.03546 | 0.02364 | 0.0326 | 0.0176 | 0.0038 |
| 8 | 0.4278 | 1.8497 | 84.4678 | 8.8604 | 3.1831 | 0.58008 | 0.38672 | 0.11994 | 0.07996 | 0.0369 | 0.0068 | 0.0008 |
| 9 | 5.6760 | 1.4579 | 85.1666 | 5.4022 | 1.5922 | 0.30366 | 0.20244 | 0.08706 | 0.05804 | 0.0385 | 0.0134 | 0.0020 |
| 10 | 0.6122 | 1.8630 | 85.4915 | 8.0626 | 2.8576 | 0.52254 | 0.34836 | 0.11412 | 0.07608 | 0.0404 | 0.0100 | 0.0016 |
| 11 | 1.6052 | 0.2339 | 95.5192 | 1.8835 | 0.4933 | 0.09108 | 0.06072 | 0.03546 | 0.02364 | 0.0326 | 0.0176 | 0.0038 |
| 12 | 0.4278 | 1.8497 | 84.4678 | 8.8604 | 3.1831 | 0.58008 | 0.38672 | 0.11994 | 0.07996 | 0.0369 | 0.0068 | 0.0008 |
| 13 | 5.6760 | 1.4579 | 85.1666 | 5.4022 | 1.5922 | 0.30366 | 0.20244 | 0.08706 | 0.05804 | 0.0385 | 0.0134 | 0.0020 |
| 14 | 0.6122 | 1.8630 | 85.4915 | 8.0626 | 2.8576 | 0.52254 | 0.34836 | 0.11412 | 0.07608 | 0.0404 | 0.0100 | 0.0016 |
| 15 | 1.6032 | 0.2299 | 95.5480 | 1.8724 | 0.4883 | 0.08982 | 0.05988 | 0.03462 | 0.02308 | 0.0312 | 0.0164 | 0.0032 |
| 16 | 0.4293 | 1.8647 | 84.4333 | 8.8669 | 3.1897 | 0.58182 | 0.38788 | 0.12066 | 0.08044 | 0.0377 | 0.0072 | 0.0004 |
| 17 | 5.6680 | 1.4349 | 85.1784 | 5.4163 | 1.5962 | 0.30426 | 0.20284 | 0.08706 | 0.05804 | 0.0387 | 0.0131 | 0.0022 |
| 18 | 0.6137 | 1.8710 | 85.4620 | 8.0768 | 2.8634 | 0.52272 | 0.34848 | 0.11412 | 0.07608 | 0.0405 | 0.0101 | 0.0011 |
| 19 | 2.3535 | 0.0401 | 92.2794 | 3.7252 | 0.9170 | 0.26166 | 0.17444 | 0.08898 | 0.05932 | 0.0654 | 0.0115 | 0.0235 |
| 20 | 2.6733 | 0.0402 | 93.0357 | 3.1217 | 0.6420 | 0.16896 | 0.11264 | 0.06930 | 0.04620 | 0.0436 | 0.0229 | 0.0235 |
| 21 | 2.4630 | 1.5280 | 90.8251 | 4.4050 | 0.6420 | 0.06774 | 0.04516 | 0.01386 | 0.00924 | 0.0003 | 0.0006 | 0.0000 |
| 22 | 0.4040 | 1.9870 | 83.9520 | 9.1380 | 3.2590 | 0.59340 | 0.39560 | 0.12540 | 0.08360 | 0.0473 | 0.0139 | 0.0008 |
| 23 | 0.4050 | 2.0270 | 83.8681 | 9.1800 | 3.2790 | 0.58560 | 0.39040 | 0.12294 | 0.08196 | 0.0459 | 0.0136 | 0.0005 |
| 24 | 0.3940 | 1.9730 | 83.7500 | 93.490 | 3.3080 | 0.58080 | 0.38720 | 0.11976 | 0.07984 | 0.0447 | 0.0133 | 0.0004 |
| 25 | 1.2630 | 1.9820 | 88.9650 | 5.4550 | 1.6160 | 0.30780 | 0.20520 | 0.09780 | 0.06520 | 0.0310 | 0.0120 | 0.0000 |
| 26 | 4.1950 | 1.5730 | 87.9810 | 4.8020 | 0.9080 | 0.18840 | 0.12560 | 0.09300 | 0.06200 | 0.0450 | 0.0260 | 0.0010 |
| 27 | 1.9080 | 1.9860 | 92.7220 | 2.7990 | 0.3430 | 0.06180 | 0.04120 | 0.06420 | 0.04280 | 0.0150 | 0.0170 | 0.0000 |
| 28 | 5.1240 | 0.5810 | 88.8020 | 4.1500 | 0.8580 | 0.17940 | 0.11960 | 0.07320 | 0.04880 | 0.0400 | 0.0220 | 0.0020 |
| 29 | 4.9480 | 1.6030 | 86.6460 | 4.9600 | 1.2440 | 0.24180 | 0.16120 | 0.08640 | 0.05760 | 0.0340 | 0.0170 | 0.0010 |
| 30 | 0.4230 | 2.1250 | 84.0050 | 8.7790 | 3.2380 | 0.64740 | 0.43160 | 0.16740 | 0.11160 | 0.0590 | 0.0130 | 0.0000 |
| 31 | 2.4750 | 1.7790 | 87.9700 | 5.5520 | 1.5120 | 0.29520 | 0.19680 | 0.09840 | 0.06560 | 0.0360 | 0.0190 | 0.0010 |
| 32 | 5.5400 | 1.7960 | 86.4450 | 4.7560 | 0.9140 | 0.19860 | 0.13240 | 0.08580 | 0.05720 | 0.0460 | 0.0260 | 0.0030 |
| 33 | 2.5050 | 0.9750 | 92.3210 | 3.2850 | 0.5690 | 0.11100 | 0.07400 | 0.06000 | 0.04000 | 0.0350 | 0.0230 | 0.0020 |
| 34 | 4.1230 | 0.7040 | 90.4400 | 3.5110 | 0.7500 | 0.17040 | 0.11360 | 0.07140 | 0.04760 | 0.0410 | 0.0250 | 0.0030 |
| 35 | 1.0370 | 2.0360 | 88.0480 | 6.2390 | 1.8390 | 0.36780 | 0.24520 | 0.09120 | 0.06080 | 0.0260 | 0.0080 | 0.0020 |
| 36 | 0.6122 | 1.8630 | 85.4915 | 8.0626 | 2.8576 | 0.52254 | 0.34836 | 0.11412 | 0.07608 | 0.0404 | 0.0100 | 0.0016 |
| 37 | 0.6137 | 1.8710 | 85.4620 | 8.0768 | 2.8634 | 0.52272 | 0.34848 | 0.11412 | 0.07608 | 0.0405 | 0.0101 | 0.0011 |
| 38 | 0.6178 | 1.9051 | 85.3453 | 8.1433 | 2.8692 | 0.53850 | 0.35900 | 0.10470 | 0.06980 | 0.0345 | 0.0117 | 0.0011 |
| 39 | 3.7924 | 0.2609 | 94.6077 | 1.0118 | 0.2128 | 0.04572 | 0.03048 | 0.01464 | 0.00976 | 0.0086 | 0.0044 | 0.0008 |
| 40 | 0.9015 | 0.0668 | 98.2722 | 0.5159 | 0.1607 | 0.03552 | 0.02368 | 0.00942 | 0.00628 | 0.0055 | 0.0016 | 0.0009 |
| 41 | 0.4313 | 1.7708 | 85.4560 | 8.4983 | 2.7421 | 0.53706 | 0.35804 | 0.10038 | 0.06692 | 0.0315 | 0.0068 | 0.0008 |
| 42 | 5.3551 | 1.7802 | 84.4784 | 5.8782 | 1.7780 | 0.34002 | 0.22668 | 0.07050 | 0.04700 | 0.0309 | 0.0116 | 0.0034 |
| 43 | 5.4939 | 1.8292 | 84.3931 | 5.8857 | 1.6910 | 0.32742 | 0.21828 | 0.06942 | 0.04628 | 0.0296 | 0.0128 | 0.0033 |
| 44 | 5.3452 | 1.7745 | 84.5143 | 5.8831 | 1.7596 | 0.33582 | 0.22388 | 0.07044 | 0.04696 | 0.0309 | 0.0119 | 0.0034 |
| 45 | 5.4952 | 1.8318 | 84.3746 | 5.8795 | 1.7111 | 0.32880 | 0.21920 | 0.06906 | 0.04604 | 0.0297 | 0.0117 | 0.0033 |
| 46 | 0.9617 | 1.5021 | 85.9284 | 8.4563 | 2.3022 | 0.41910 | 0.27940 | 0.07308 | 0.04872 | 0.0228 | 0.0057 | 0.0005 |
| 47 | 0.4264 | 1.9201 | 84.3789 | 8.8749 | 3.1776 | 0.60132 | 0.40088 | 0.10872 | 0.07248 | 0.0310 | 0.0065 | 0.0012 |
| 48 | 1.2010 | 1.8560 | 88.2210 | 6.1190 | 1.8840 | 0.35340 | 0.23560 | 0.05580 | 0.03720 | 0.0230 | 0.0130 | 0.0010 |
| 49 | 0.3407 | 1.8816 | 83.4187 | 9.5284 | 3.5694 | 0.62190 | 0.41460 | 0.10968 | 0.07312 | 0.0327 | 0.0081 | 0.0011 |

TABLE I-continued

| | nitrogen [mole %] | carbon dioxide [mole %] | methane [mole %] | ethane [mole %] | propane [mole %] | 1-butane [mole %] | n-butane [mole %] | 1-pentane [mole %] | n-pentane [mole %] | n-hexane [mole %] | n-heptane [mole %] | n-octane [mole %] |
|---|---|---|---|---|---|---|---|---|---|---|---|---|
| 50 | 5.9990 | 1.3984 | 84.4872 | 5.9271 | 1.5364 | 0.30534 | 0.20356 | 0.06342 | 0.04228 | 0.0251 | 0.0101 | 0.0021 |
| 51 | 1.4200 | 0.0330 | 93.3240 | 1.7800 | 3.2000 | 0.08700 | 0.05800 | 0.02520 | 0.01680 | 0.0560 | 0.0000 | 0.0000 |
| 52 | 1.9285 | 0.4422 | 84.3361 | 8.8946 | 3.1919 | 0.59064 | 0.39376 | 0.10950 | 0.07300 | 0.0325 | 0.0061 | 0.0012 |
| 53 | 0.2331 | 1.6004 | 95.5340 | 1.8790 | 0.4926 | 0.09066 | 0.06044 | 0.03522 | 0.02348 | 0.0309 | 0.0168 | 0.0034 |
| 54 | 1.4546 | 5.6769 | 85.1473 | 5.4174 | 1.5968 | 0.30438 | 0.20292 | 0.08694 | 0.05796 | 0.0391 | 0.0138 | 0.0019 |
| 55 | 1.8643 | 0.6224 | 85.4814 | 8.0607 | 2.8624 | 0.52170 | 0.34780 | 0.11346 | 0.07564 | 0.0398 | 0.0096 | 0.0008 |
| 56 | 1.8292 | 5.4939 | 84.3931 | 5.8857 | 1.6910 | 0.32742 | 0.21828 | 0.06942 | 0.04628 | 0.0296 | 0.0128 | 0.0033 |
| 57 | 1.7802 | 5.3551 | 84.4786 | 5.8782 | 1.7778 | 0.34002 | 0.22668 | 0.07050 | 0.04700 | 0.0309 | 0.0116 | 0.0034 |
| 58 | 0.2339 | 1.6052 | 95.5192 | 1.8835 | 0.4933 | 0.09108 | 0.06072 | 0.03546 | 0.02364 | 0.0326 | 0.0176 | 0.0038 |
| 59 | 1.8497 | 0.4278 | 84.4678 | 8.8604 | 3.1831 | 0.58008 | 0.38672 | 0.11994 | 0.07996 | 0.0369 | 0.0068 | 0.0008 |
| 60 | 1.4579 | 5.6760 | 85.1666 | 5.4022 | 1.5922 | 0.30366 | 0.20244 | 0.08706 | 0.05804 | 0.0385 | 0.0134 | 0.0020 |
| 61 | 1.8630 | 0.6122 | 85.4915 | 8.0626 | 2.8576 | 0.52254 | 0.34836 | 0.11412 | 0.07608 | 0.0404 | 0.0100 | 0.0016 |
| 62 | 0.2339 | 1.6052 | 95.5192 | 1.8835 | 0.4933 | 0.09108 | 0.06072 | 0.03546 | 0.02364 | 0.0326 | 0.0176 | 0.0038 |
| 63 | 1.8497 | 0.4278 | 84.4678 | 8.8604 | 3.1831 | 0.58008 | 0.38672 | 0.11994 | 0.07996 | 0.0369 | 0.0068 | 0.0008 |
| 64 | 1.4579 | 5.6760 | 85.1666 | 5.4022 | 1.5922 | 0.30366 | 0.20244 | 0.08706 | 0.05804 | 0.0385 | 0.0134 | 0.0020 |
| 65 | 1.8630 | 0.6122 | 85.4915 | 8.0626 | 2.8576 | 0.52254 | 0.34836 | 0.11412 | 0.07608 | 0.0404 | 0.0100 | 0.0016 |
| 66 | 0.2299 | 1.6032 | 95.5480 | 1.8724 | 0.4883 | 0.08982 | 0.05988 | 0.03462 | 0.02308 | 0.0312 | 0.0164 | 0.0032 |
| 67 | 1.8647 | 0.4293 | 84.4333 | 8.8669 | 3.1897 | 0.58182 | 0.38788 | 0.12066 | 0.08044 | 0.0377 | 0.0072 | 0.0004 |
| 68 | 1.4349 | 5.6680 | 85.1784 | 5.4163 | 1.5962 | 0.30426 | 0.20284 | 0.08706 | 0.05804 | 0.0387 | 0.0131 | 0.0022 |
| 69 | 1.8710 | 0.6137 | 85.4620 | 8.0768 | 2.8634 | 0.52272 | 0.34848 | 0.11412 | 0.07608 | 0.0405 | 0.0101 | 0.0011 |
| 70 | 0.0401 | 2.3535 | 92.2794 | 3.7252 | 0.9170 | 0.26166 | 0.17444 | 0.08898 | 0.05932 | 0.0654 | 0.0115 | 0.0235 |
| 71 | 0.0402 | 2.6733 | 93.0357 | 3.1217 | 0.6420 | 0.16896 | 0.11264 | 0.06930 | 0.04620 | 0.0436 | 0.0229 | 0.0235 |
| 72 | 1.5280 | 2.4630 | 90.8251 | 4.4050 | 0.6420 | 0.06774 | 0.04516 | 0.01386 | 0.00924 | 0.0003 | 0.0006 | 0.0000 |
| 73 | 1.9870 | 0.4040 | 83.9520 | 9.1380 | 3.2590 | 0.59340 | 0.39560 | 0.12540 | 0.08360 | 0.0473 | 0.0139 | 0.0008 |
| 74 | 2.0270 | 0.4050 | 83.8681 | 9.1800 | 3.2790 | 0.58560 | 0.39040 | 0.12294 | 0.08196 | 0.0459 | 0.0136 | 0.0005 |
| 75 | 1.9730 | 0.3940 | 83.7500 | 9.3490 | 3.3080 | 0.58080 | 0.38720 | 0.11976 | 0.07984 | 0.0447 | 0.0133 | 0.0004 |
| 76 | 1.9820 | 1.2630 | 88.9650 | 5.4550 | 1.6160 | 0.30780 | 0.20520 | 0.09780 | 0.06520 | 0.0310 | 0.0120 | 0.0000 |
| 77 | 1.5730 | 4.1950 | 87.9810 | 4.8020 | 0.9080 | 0.18840 | 0.12560 | 0.09300 | 0.06200 | 0.0450 | 0.0260 | 0.0010 |
| 78 | 1.9860 | 1.9080 | 92.7220 | 2.7990 | 0.3430 | 0.06180 | 0.04120 | 0.06420 | 0.04280 | 0.0150 | 0.0170 | 0.0000 |
| 79 | 0.5810 | 5.1240 | 88.8020 | 4.1500 | 0.8580 | 0.17940 | 0.11960 | 0.07320 | 0.04880 | 0.0400 | 0.0220 | 0.0020 |
| 80 | 1.6030 | 4.9480 | 86.6460 | 4.9600 | 1.2440 | 0.24180 | 0.16120 | 0.08640 | 0.05760 | 0.0340 | 0.0170 | 0.0010 |
| 81 | 2.1250 | 0.4230 | 84.0050 | 8.7790 | 3.2380 | 0.64740 | 0.43160 | 0.16740 | 0.11160 | 0.0590 | 0.0130 | 0.0000 |
| 82 | 1.7790 | 2.4750 | 87.9700 | 5.5520 | 1.5120 | 0.29520 | 0.19680 | 0.09840 | 0.06560 | 0.0360 | 0.0190 | 0.0010 |
| 83 | 1.7960 | 5.5400 | 86.4450 | 4.7560 | 0.9140 | 0.19860 | 0.13240 | 0.08580 | 0.05720 | 0.0460 | 0.0260 | 0.0030 |
| 84 | 0.9750 | 2.5050 | 92.3210 | 3.2850 | 0.5690 | 0.11100 | 0.07400 | 0.06000 | 0.04000 | 0.0350 | 0.0230 | 0.0020 |
| 85 | 0.7040 | 4.1230 | 90.4400 | 3.5110 | 0.7500 | 0.17040 | 0.11360 | 0.07140 | 0.04760 | 0.0410 | 0.0250 | 0.0030 |
| 86 | 2.0360 | 1.0370 | 88.0480 | 6.2390 | 1.8390 | 0.36780 | 0.24520 | 0.09120 | 0.06080 | 0.0260 | 0.0080 | 0.0020 |
| 87 | 1.8630 | 0.6122 | 85.4915 | 8.0626 | 2.8576 | 0.52254 | 0.34836 | 0.11412 | 0.07608 | 0.0404 | 0.0100 | 0.0016 |
| 88 | 1.8710 | 0.6137 | 85.4620 | 8.0768 | 2.8634 | 0.52272 | 0.34848 | 0.11412 | 0.07608 | 0.0405 | 0.0101 | 0.0011 |
| 89 | 1.9051 | 0.6178 | 85.3453 | 8.1433 | 2.8692 | 0.53850 | 0.35900 | 0.10470 | 0.06980 | 0.0345 | 0.0117 | 0.0011 |
| 90 | 0.2609 | 3.7924 | 94.6077 | 1.0118 | 0.2128 | 0.04572 | 0.03048 | 0.01464 | 0.00976 | 0.0086 | 0.0044 | 0.0008 |
| 91 | 0.0668 | 0.9015 | 98.2722 | 0.5159 | 0.1607 | 0.03552 | 0.02368 | 0.00942 | 0.00628 | 0.0055 | 0.0016 | 0.0009 |
| 92 | 1.7708 | .04313 | 85.4560 | 8.4983 | 2.7421 | 0.53706 | 0.35804 | 0.10038 | 0.06692 | 0.0315 | 0.0068 | 0.0008 |
| 93 | 1.7802 | 5.3551 | 84.4784 | 5.8782 | 1.7780 | 0.34002 | 0.22668 | 0.07050 | 0.04700 | 0.0309 | 0.0116 | 0.0034 |
| 94 | 1.8292 | 5.4939 | 84.3931 | 5.8857 | 1.6910 | 0.32742 | 0.21828 | 0.06942 | 0.04628 | 0.0296 | 0.0128 | 0.0033 |
| 95 | 1.7745 | 5.3452 | 84.5143 | 5.8831 | 1.7596 | 0.33582 | 0.22388 | 0.07044 | 0.04696 | 0.0309 | 0.0119 | 0.0034 |
| 96 | 1.8318 | 5.4952 | 84.3746 | 5.8795 | 1.7111 | 0.32880 | 0.21920 | 0.06906 | 0.04604 | 0.0297 | 0.0117 | 0.0033 |
| 97 | 1.5021 | 0.9617 | 85.9284 | 8.4563 | 2.3022 | 0.41910 | 0.27940 | 0.07308 | 0.04872 | 0.0228 | 0.0057 | 0.0005 |
| 98 | 1.9201 | 0.4264 | 84.3789 | 8.8749 | 3.1776 | 0.60132 | 0.40088 | 0.10872 | 0.07248 | 0.0310 | 0.0065 | 0.0012 |
| 99 | 1.8560 | 1.2010 | 88.2210 | 6.1190 | 1.8840 | 0.35340 | 0.23560 | 0.05580 | 0.03720 | 0.0230 | 0.0130 | 0.0010 |
| 100 | 1.8816 | 0.3407 | 83.4187 | 9.5284 | 3.5694 | 0.62190 | 0.41460 | 0.10968 | 0.07312 | 0.0327 | 0.0081 | 0.0011 |
| 101 | 1.3984 | 5.9990 | 84.4872 | 5.9271 | 1.5364 | 0.30534 | 0.20356 | 0.06342 | 0.04228 | 0.0251 | 0.0101 | 0.0021 |
| 102 | 0.0330 | 1.4200 | 93.3240 | 1.7800 | 3.2000 | 0.08700 | 0.05800 | 0.02520 | 0.01680 | 0.0560 | 0.0000 | 0.0000 |

Model Equations for Thermodynamic Properties

The values for $M$, $H_m$, $\rho_{std}$, and $H_{n,ref}$ can be calculated using the model equations shown below, and the composition values from Table I for each natural gas composition.

$$M = \sum_{i=1}^{N} \left( \frac{X_i}{100} M_i \right) \quad [1\text{-}4]$$

where N is the number of pure gas components in the mixture, $X_i$ is the mole percentage of each component, and $M_i$ is the molecular weight of each component (from the Gas Processor's Association (GPA) Standard 2145 (1994)).

$$H_m = \frac{\sum_{i=1}^{N} \left( \frac{X_i}{100} M_i H_{m,i} \right)}{M} \quad [1\text{-}5]$$

where N is the number of pure gas components in the mixture, $X_i$ is the mole percentage of each component, $M_i$ is the molecular weight of each component, and $H_{m,i}$ is the mass-based heating value of each component (from the GPA) Standard 2145 (1994). In the natural gas industry, it is standard practice to use chemical enthalpies (heating values) determined at standard conditions of 60° F. and 14.696 psia, even though the volumetric basis is often converted to a pressure of 14.73 psia. The GPA Standard 2145 (1994) provides the $H_{m,i}$ data at the accepted chemical enthalpy conditions of 60° F. and 14.696 psia.

$$\rho_{std} = \frac{P_{std}M}{ZRT_{std}} \quad [1\text{-}6]$$

In this case, the real gas state equation is used, where $P_{std}$ and $T_{std}$ are standard pressure and temperature (absolute units), M is the mixture molecular weight, Z is the compressibility factor, and R is the universal gas constant. Since $P_{std}$, $T_{std}$, and R are all constants, $\rho_{std}$ is a function of only the variable ratio M/Z.

$$H_{n,ref} = \sum_{i=1}^{N} \left( \frac{X_i}{100} H_{n,ref,i} \right) \quad [1\text{-}7]$$

where $X_i$ is the mole percentage of each pure gas component, and $H_{n,ref,i}$ is the molar ideal gross heating value (at 25° C. and 0.101325 MPa) of each pure gas component (from American Gas Association (A.G.A.) Transmission Committee Report 8 (1994)).

Assuming three inferential gas characterization properties are known, namely, the speed of sound at 60° F. and 14.73 psia, $S_{std}$[ft/s], the carbon dioxide concentration, $X_{CO2}$ [mol %], and the nitrogen concentration, $X_{N2}$[mol %], and that the Mixture Molecular Weight, M, has a quadratic relationship with respect to the standard sound speed, $S_{std}$, such that the $S_{std}$ can be calculated using the commercially available SonicWare™ software or the GRI Extended Thermodynamic Properties Computer Programs (Gas Research Institute 1989, unpublished) at 60° F. and 14.73 psia, the form of the inferential correlation may be chosen as:

$$M = A + BS_{std} + CS_{std}^2 \quad [1\text{-}8]$$

where: $A = A_0 + A_1 X_{N2} + A_2 X_{CO2}$, $B = B_0 + B_1 X_{N2} + B_2 X_{CO2}$, and $C = C_0 + C_1 X_{N2} + C_2 X_{CO2}$. A least squares curve fit of the data in Table 1 produces the following values for the unknown constants: $A_0 = 89.59987$, $A_1 = 0.2595616$, $A_2 = 0.8420112$, $B_0 = -0.08303539$, $B_1 = -3.57614 \times 1031$ 4, $B_2 = -1.20199 \times 10^{-3}$, $C_0 = 2.22787 \times 10^{-5}$, $C_1 = 1.37342 \times 10^{-7}$, and $C_2 = 4.51462 \times 10^{-7}$.

Assuming knowledge of the same inferential gas characterization properties, that $H_{m,CO2} = H_{m,N2} = 0$ (i.e., that diluent gases have no heating value), and that $H_m$ is a weak function of hydrocarbon composition, the Hydrocarbon Molecular Weight, $M_{HC}$, may be defined as:

$$M_{HC} = M - \left( \frac{X_{CO2}}{100} M_{CO2} \right) - \left( \frac{X_{N2}}{100} M_{N2} \right) \quad [1\text{-}9]$$

And the form of the inferential correlation may be chosen as:

$$H_m = \left( \frac{A + BM_{HC}}{M} \right) \quad [1\text{-}10]$$

where: $B = B_0 + B_1 S_{std}$ and $B_1 = B_2 + B_3 X_{N2} + B_4 X_{CO2}$. A least squares curve fit of the data in Table 1 produces values for the unknown constants: $A = 54{,}343.048$, $B_0 = 20{,}442.406$, $B_2 = 0.04552871$, $B_3 = -0.02523803$, and $B_4 = -0.02568212$.

Even though gas density is, in general, a thermodynamic property, the standard density is a chemical property because it is evaluated at specific conditions of 60° F., 14.73 psia, and at the flowing gas composition.

Because M has already been correlated to inferential properties (See equation 1-8]), and Z varies only about 0.1% across the Table 1 database compositions due to the low-pressure standard condition, the form of the standard density correlation is straightforward. Therefore, the same correlation form as equation [1-8] may be used to determine unique correlation constants for standard density:

$$\rho_{std} = A + BS_{std} + CS_{std}^2 \quad [1\text{-}11]$$

where: $A = A_0 + A_1 X_{N2} + A_2 X_{CO2}$, $B = B_0 + B_1 X_{N2} + B_2 X_{CO2}$, and $C = C_0 + C_1 X_{N2} + C_2 X_{CO2}$. A least squares fit to the database of Table 1 produced values for the unknown constants: $A_0 = 0.2395147$, $A_1 = 7.067074 \times 1031$ 4, $A_2 = 2.334917 \times 10^{-3}$, $B_0 = -2.228333 \times 10^{-4}$, $B_1 = -9.87042 \times 10^{-7}$, $B_2 = -3.35135 \times 10^{-6}$, $C_0 = 5.99480 \times 10^{-8}$, $C_1 = 3.81330 \times 10^{-10}$, and $C_2 = 1.26106 \times 10^{-9}$.

The Molar Ideal Gross Heating Value, at 25° C. and 0.101325 MPa reference conditions, is important as an intermediate variable that may be used to characterize natural gas composition for density calculations.

The form of the data correlation to inferential variables is chosen to be the same as that for the mass-based heating value, $H_m$, which is also a molar ideal gross heating value at a different reference state, using different units:

$$H_{n,ref} = A + BM_{HC} \quad [1\text{-}12]$$

where: $B = B_0 + B_1 S_{std}$, and $B_1 = B_2 + B_3 X_{N2} + B_4 X_{CO2}$. A least squares curve fit of the data in the Table 1 database produces values for the unknown constants: $A = 123.81271$, $B_0 = 47.41274$, $B_2 = 2.73661 \times 10^{-4}$, $B_3 = -5.71187 \times 10^{-5}$, $B_4 = -5.73574 \times 10^{-5}$.

Thermodynamic properties are more difficult to characterize than chemical properties because chemical property dependence must be modeled as a function of temperature and pressure. As discussed with respect to various flow meters, gas density, $\rho$, is the most important thermodynamic property related to natural gas energy flow measurement. The isentropic exponent, $\kappa$, and viscosity, $\mu$, are required for differential-based meters, but are less important because they form a part of less sensitive terms (the isentropic exponent is needed for the expansion factor, and viscosity is needed for the Reynolds number). Thus, it is important to be able to correlate gas density, $\rho$, to the pre-selected inferential properties of standard sound speed, $S_{std}$, carbon dioxide concentration, $X_{CO2}$, nitrogen concentration, $X_{N2}$, and, as noted above, the temperature, T, and pressure, P.

The U.S. natural gas industry currently has two well-accepted equations of state for computing natural gas density (i.e., the compressibility factor). These are contained in the A.G.A. Transmission Measurement Committee Report 8 (1994), referenced and included as if set forth entirely herein, and denominated as: the Detailed Characterization Method, which requires a detailed gas composition assay to characterize the gas, and the Gross Characterization Method, which requires inferential properties to characterize the gas. Both methods specify an uncertainty level of 0.1% over 32–130° F., up to 1200 psia, and gas compositions in the "normal range" detailed in Table 2.

TABLE 2

| Quantity | Normal Range |
|---|---|
| Relative Density* | 0.554–0.87 |
| Gross Heating Value** [Btu/scf] | 447–1,150 |
| Gross Heating Value*** [MJ/m³] | 18.7–45.1 |
| Methane [mol %] | 45.0–100.0 |
| Nitrogen [mol %] | 0–50.0 |
| Carbon Dioxide [mol %] | 0–30.0 |

TABLE 2-continued

| Quantity | Normal Range |
| --- | --- |
| Ethane [mol %] | 0–10.0 |
| Propane [[mol %] | 0–4.0 |
| Total Butanes [mol %] | 0–1.0 |
| Total Pentanes [mol %] | 0–0.3 |
| Hexanes Plus [mol %] | 0–0.2 |
| Helium [mol %] | 0–0.2 |
| Hydrogen [mol %] | 0–10.0 |
| Carbon Monoxide [mol %] | 0–3.0 |
| Water [mol %] | 0–0.05 |
| Hydrogen Sulfide [mol %] | 0–0.02 |

*Reference Condition: Relative density at 60° F., 14.73 psia
**Reference Conditions: Combustion at 60° F., 14.73 psia; density at 60° F., 14.73 psia.
***Reference Conditions: Combustion at 25° C., 0.101325 MPa; density at 0° C., 0.101325 MPa.

The current Gross Characterization Method allows the user to characterize a gas using one of two inferential variable sets: volumetric gross heating value, relative density, and carbon dioxide concentration (Method 1); or relative density, carbon dioxide concentration, and nitrogen concentration (Method 2). This invention introduces a new variable set: standard sound speed, $S_{std}$, carbon dioxide concentration, $X_{CO2}$, and nitrogen concentration, $X_{N2}$ (designated hereinafter as "Method 3").

The Gross Characterization Method is a virial equation of state, and is cast in terms of compressibility factor, Z, as a truncated expansion of molar density, d:

$$Z(T, P, composition) = \frac{\rho_{idealgas}}{\rho_{realgas}} = 1 + B_{mix}d + C_{mix}d^2 \quad [1\text{-}13]$$

where compressibility factor, Z, is a dimensionless density, d is the molar density (a function of T, P, and composition), and the virial coefficients, $B_{mix}$ and $C_{mix}$, are complicated functions of temperature and composition. Since Z and d are both functions of temperature, T, pressure, P, and composition, the solution of Equation [1-13] is iterative.

The Gross Characterization method determines the virial coefficients, $B_{mix}$ and $C_{mix}$ by modeling the natural gas as a three component mixture containing carbon dioxide, nitrogen, and an equivalent hydrocarbon component. The equivalent hydrocarbon component is then characterized by one of the two inferential variable sets, using them to determine a single hydrocarbon characterization parameter, $H_{CH}$, which is the molar ideal gross heating value of the equivalent hydrocarbon [kJ/mol at reference conditions of 25° C. and 0.101325 MPa]. $H_{CH}$ is related to $H_{n,ref}$ by the following equation:

$$H_{CH} = \frac{H_{n,ref}}{\left(1 - \left(\frac{X_{CO2} + X_{N2}}{100}\right)\right)} \quad [1\text{-}14]$$

Since $H_{n,ref}$ has already been correlated to $S_{std}$, $X_{CO2}$, and $X_{N2}$ in Equation [1-12], $H_{CH}$ is now known as a function of the pre-selected inferential variables $S_{std}$, $X_{CO2}$, and $X_{N2}$, and can be used to characterize the equivalent hydrocarbon group for Method 3 of the Gross Characterization Method.

The most accurate way to determine $H_{CH}$ is from the detailed gas composition assay using Equations [1-7] and [1-14], but doing so defeats the purpose of gross inferential characterization. However, it is useful as a mechanism to verify the validity of the inferential characterization approach (i.e., Method 3) using the database of natural gas compositions in Table 1. Calculating natural gas density using both approaches over the entire temperature and pressure range of the A.G.A. Gross Characterization Method of Committee Report 8 provides two sets of residuals which agree within about ±0.05%.

Thermodynamic Properties from Sound Speed at Standard Temperature and Pressure

Figure 2:
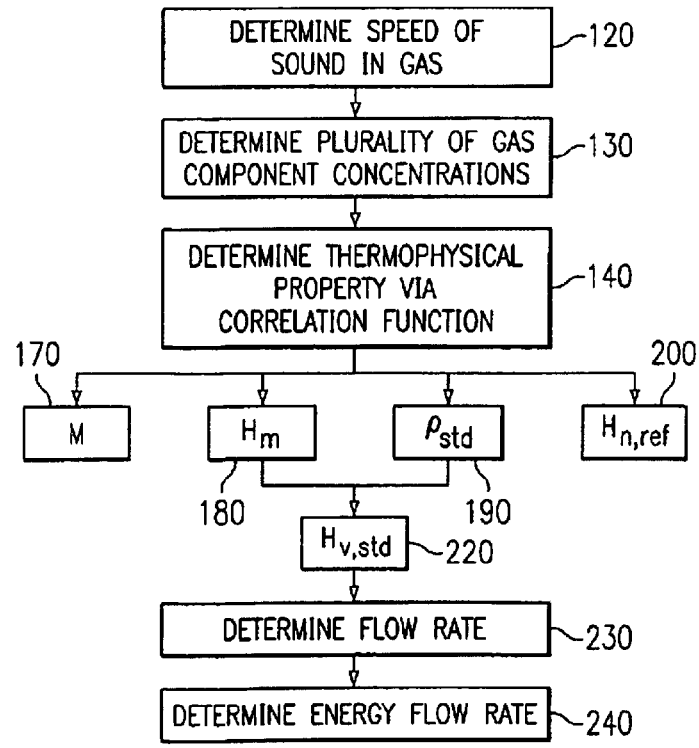
FIG. 2 is a flow diagram illustrating the method of determining thermophysical properties of a gas according to the present invention.

FIG. 2 is a flow chart summarizing the method 100 of the present invention. The method begins with determining the speed of sound in step 120. Once the speed of sound in the gas is determined, it is necessary to determine a plurality (two or more) of concentrations for various non-combustible components which comprise the gas in step 130. Examples using the concentrations of carbon dioxide and nitrogen concentration have been explicitly detailed. The thermophysical property determination via correlation in step 140 is then effected by an empirical process, as discussed in detail above.

The inferential correlation for various chemical properties may be determined, including mixture molecular weight (M) in step 170, mass-based heating value ($H_m$) in step 180, standard density ($\rho_{STD}$) in step 190, mixture molar ideal gross heating value ($H_{n,ref}$) in step 200. Other properties may also be determined, such as molar specific heat at constant volume ($c_v$), molar specific heat at constant pressure ($c_p$), and the ratio of specific heats $\kappa = c_p/c_v$.

As has been noted, the standard heating value ($H_{v,std}$) can be calculated from the mass-based heating value, $H_m$, and the standard density, $\rho_{STD}$. This is accomplished in step 220. If the flow rate is determined in step 230, then the energy flow rate, which is the product of the standard heating value ($H_{v,std}$) and the flow rate ($Q_{v,std}$), can be determined in step 240, as shown above.

In summary, the method for determining thermophysical properties of a multi-component gas described above is based upon measuring the speed of sound in the natural gas mixture at standard pressure (14.73 psia) and standard temperature (60° F.), along with the molar concentrations of nitrogen, $X_{N2}$, and carbon dioxide, $X_{CO2}$. Since the speed of sound at standard pressure and temperature is related to the relative density of the natural gas mixture (the ratio of the natural gas mixture density to the air density) at standard pressure and temperature, it can be used in place of the relative density in the Gross Characterization Method of the A.G.A. Report no. 8 equation of state (designated as Method 3 above) to calculate the density and properties of the gas at flowing temperature and pressure.

Thermodynamic Properties from Sound Speed at Arbitrary Temperature and Pressure

Figure 3:
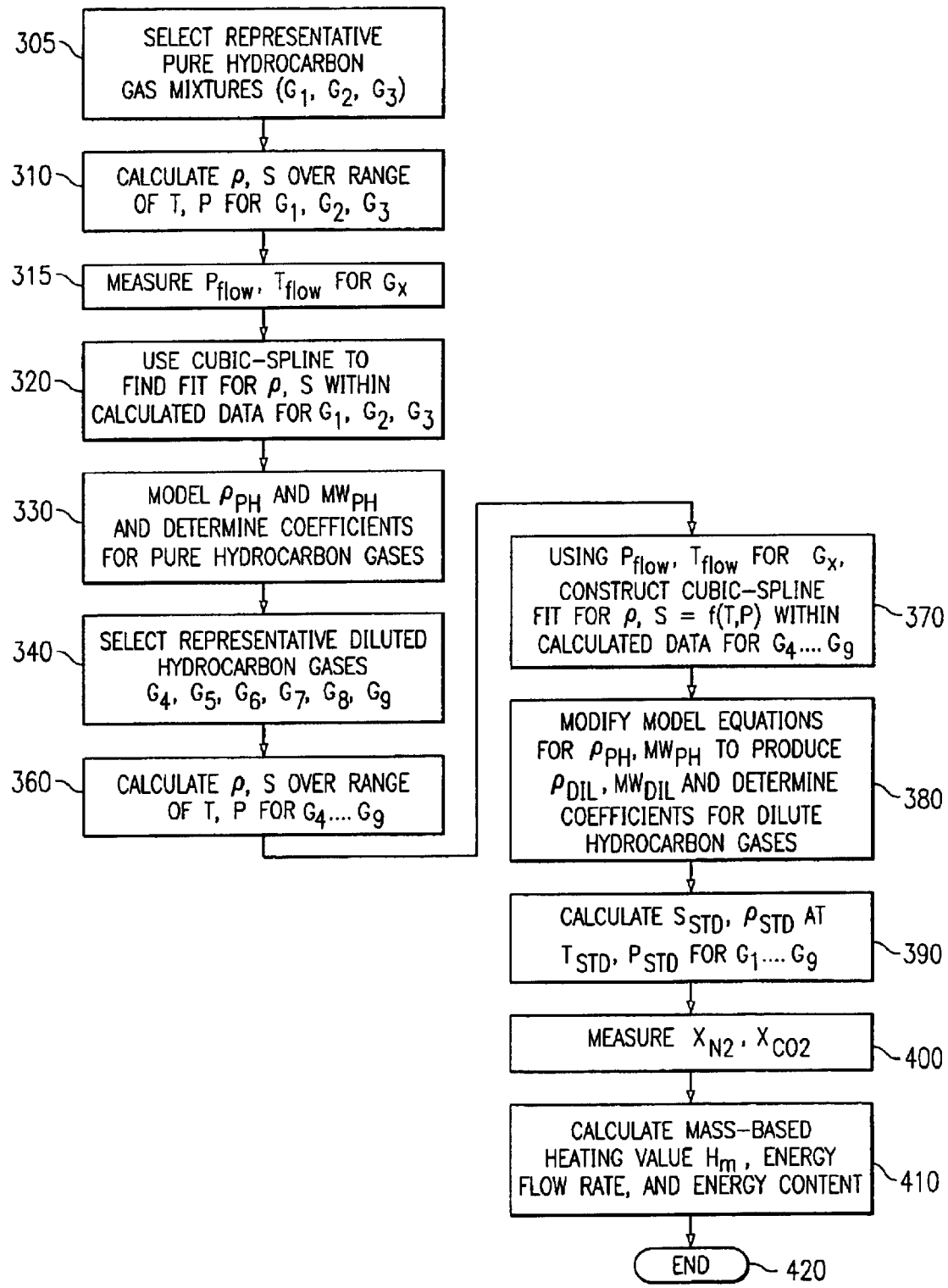
FIG. 3 illustrates an alternative embodiment of the method of the present invention, which is based on properties of the gas at any arbitrary temperature and pressure.

FIG. 3 illustrates a method for determining thermodynamic properties based on speed of sound measurements that are not necessarily at standard pressure and temperature. This method permits an energy meter module that is compatible with conventional ultrasonic flow meters, which measure the speed of sound in flowing gas at arbitrary (i.e., pipeline) pressure and temperature.

In step 305, three reference natural gas mixtures $G_1$, $G_2$, and $G_3$ are selected that cover the range of interest in natural gas molecular weight (MW). Each selected gas mixture is a "pure hydrocarbon" gas mixture, in that it comprises hydrocarbon gases only and no diluents. In other words, their diluent concentrations are 0.0 mole % carbon dioxide and 0.0 mole % nitrogen.

For purposes of example herein, the reference gas mixtures are those identified in Table 1 as ID# 40, 26, and 49. Each of the reference gas mixtures has no nitrogen or carbon dioxide component, and are identified as Gas ID#40_00_

00=$G_1$, Gas ID#26__00__00=$G_2$, and Gas ID#49__00__00= $G_3$. The digits __00__00 after the Gas ID# indicate that the mole % concentrations of carbon dioxide and nitrogen are equal to zero. Using standard calculations known in the art, the reference gas mixtures $G_1$, $G_2$, and $G_3$ are found to have molecular weights of MW1=16.202, MW2=17.318 and MW3=19.017 respectively.

In step 310, a computer process (which may be a computer program such as SonicWare™ software) is used to calculate values of the density, ρ, and the speed of sound, S, for a matrix of values of gas temperature, T, and gas pressure, P, for $G_1$, $G_2$, and $G_3$. For example, the temperature values may range from about 20° F. to about 150° F. in steps of 10° F. Pressure values may include 14.73 psia, 50 psia, 100 psia, and a range of steps from 100 psia to 1400 psia, in steps of 100 psia. The calculated values of ρ, S, T, and P are formatted as a look up table, which is then stored in the processor 80 memory.

The subject of the method of FIG. 3 is a natural gas mixture, $G_x$, (whose composition is to be estimated) flowing in a pipeline. In Step 315, the pressure and temperature of the subject gas mixture are measured and recorded as $P_{flow}$, and $T_{flow}$.

In Step 320, the recorded data for the three reference gas mixtures $G_1$, $G_2$, and $G_3$ is used with a cubic-spline fit algorithm to provide numerical (approximate) fits for density and the speed of sound as a function of temperature and pressure, using the measured values $P_{flow}$ and $T_{flow}$. The result is three pairs of values for the speed of sound and density ($S_1$, ρ1), ($S_2$, ρ2) and ($S_3$, ρ3) corresponding to the three pure hydrocarbon gas mixtures $G_1$, $G_2$, and $G_3$ at the measured $P_{flow}$ and $T_{flow}$.

The use of a look up table and interpolation, as performed in Steps 310 and 320, permits the calculations to be done prior to the run time process of FIG. 3. However, as an alternative to Steps 310 and 320, the values for the speed of sound and density may be calculated "on the fly". This requires that appropriate software, such as Sonic Ware, or a similar program, be embedded (or be otherwise available) during the processing for the method of FIG. 3.

In step 330, the variation of density with speed of sound for a pure hydrocarbon natural gas mixture is modeled using a second order (quadratic) equation. The form of the equation is:

$$\rho_{PH} = AP + \frac{BP}{S} + \frac{CP}{S^2}, \qquad [1\text{-}18]$$

where S is the speed of sound. The values of the coefficients, AP, BP, and CP are determined from the values of ($S_1$, ρ1), ($S_2$, ρ2) and ($S_3$, ρ3) (derived as discussed above in connection with in step 320 by interpolation or calculation).

The variation in molecular weight of the reference gas mixtures as a function of speed of sound is also modeled as a second order equation. The form of this equation is:

$$MW_{PH} = AMW + \frac{BMW}{S} + \frac{CMW}{S^2} \qquad [1\text{-}19]$$

The values of the coefficients AMW, BMW and CMW are then determined using the known/derived values of (MW1, $S_1$), (MW2,$S_2$) and (MW3,$S_3$) for the gas mixtures $G_1$, $G_2$, and G3. The molecular weight values were calculated in step 305. The fully determined equations [1-18] and [1-19] now provide a mechanism to calculate, at arbitrary temperature and pressure, the density and the molecular weight of a natural gas mixture that does not contain diluents.

To account for the effect of natural gas diluents on density and molecular weight, additional reference data, representative of gas mixtures containing nitrogen and carbon dioxide, must be developed. Therefore, in Step 340, six additional reference gas mixtures are selected. These may be based upon varying the compositions of the pure hydrocarbon mixtures identified as ID#40__00__00=$G_1$, Gas ID#26__ 00__00=$G_2$, and Gas ID#49__00__00=$G_3$ are selected. For example, using the gas mixture designated Gas ID#40__00__ 00, the concentration of each hydrocarbon gas component in the Table 1 ID# 40 gas mixture can be multiplied by a factor of 0.94, and 2.0 mole % of carbon dioxide and 4.0 mole % of nitrogen can be added to form a new (dilute) gas mixture, designated as Gas ID#40__02__04=$G_4$. Another gas mixture can be formed by replacing the 2.0 mole % of carbon dioxide with 4.0 mole % of carbon dioxide, and the 4.0 mole % of nitrogen with 2.0 mole % of nitrogen (using the same multiplication factor 0.94 to scale down the original mixture). This produces a new dilute gas mixture identified as Gas ID#40__04__02=$G_5$. In a similar manner, four more gas mixtures identified as Gas ID#26__02__04=$G_6$, Gas ID#26__04__02=$G_7$, Gas ID#49__02__04=$G_8$, and Gas ID#49__ 04__02=$G_9$ can be formulated. The molecular weights for these six new gas mixtures can be calculated using standard methods known in the art. The resulting MW values for the mixtures $G_4$, $G_5$, $G_6$, $G_7$, $G_8$, and $G_9$ are MW4=17.230, MW5=17.550, MW6=18.280, MW7= 18.600, MW8=19.876 and MW9=20.196, respectively.

In step 360, a computer process (similar or identical to SonicWare™ software) is used to calculate values of the gas mixture density, ρ, and the speed of sound, S, over a range of values for gas temperature, T, and gas pressure, P, for the gas mixtures $G_4$ $G_5$, $G_6$, $G_7$, $G_8$, and $G_9$. Step 360 is similar to step 310. The values of ρ, S, T, and P are then saved as six data files in the processor 80 memory.

In Step 370, in a manner similar to Step 320, the stored data files for gas mixtures $G_4$, $G_5$, $G_6$, $G_7$, $G_8$, and $G_9$ are used to provide numerical fits for density and speed of sound as functions of temperature and pressure in the vicinity of the measured $P_{flow}$ and $T_{flow}$, using a cubic-spline fit algorithm. The result is six pairs of speed of sound and gas mixture density values ($S_4$,ρ4), ($S_5$,ρ5), ($S_6$,ρ6), ($S_7$,ρ7), ($S_8$,ρ8) and ($S_9$,ρ9) corresponding to the diluted gas mixtures $G_4$, $G_5$, $G_6$, $G_7$, $G_8$, and $G_9$.

As with Steps 310 and 320, Steps 360 and 370 can be eliminated by directly calculating density and speed of sound at the measured temperature and pressure. As discussed above, the direct calculation requires the use of appropriate software rather than look up tables and interpolation.

In Step 380, the model equations for $\rho_{pH}$ and $MW_{pH}$ are modified to include the effect of the natural gas diluents N2 and CO2. The new form of the equation for ρ is:

$$\rho_{dil} = \left(AP + \frac{BP}{S} + \frac{CP}{S^2}\right) * \qquad [1\text{-}20]$$
$$\left(1 + \left(D1 + \frac{D2}{S} + \frac{D3}{S^2}\right) * XCO_2 + \left(E1 + \frac{E2}{S} + \frac{E3}{S^2}\right) * XN_2\right),$$

where $XCO_2$ is the mole % of carbon dioxide and $XN_2$ is the mole % of nitrogen. The values of AP, BP and CP were determined in step 330. The six new coefficients, D1, D2, D3 and E1, E2 and E3 can be calculated by substituting the pairs of values ($S_4$,ρ4) through ($S_9$,ρ9) into this equation and using matrix algebra operations to solve the six simultaneous equations for the coefficients. The resulting fully-determined equation [1-20] models density as a function of temperature, pressure, speed of sound, mole % of carbon dioxide, and mole % of nitrogen measured at flowing pressure and temperature.

Similarly, an equation for molecular weight as a function of the speed of sound and the mole % concentrations of carbon dioxide and nitrogen can be formed as follows:

$$MW_{dil} = \left(AMW + \frac{BMW}{S} + \frac{CMW}{S^2}\right) * \qquad [1\text{-}21]$$
$$\left(1 + \left(DM1 + \frac{DM2}{S} + \frac{DM3}{S^2}\right) * XCO_2 + \right.$$
$$\left.\left(EM1 + \frac{EM2}{S} + \frac{EM3}{S^2}\right) * XN_2\right)$$

The values of coefficients AMW, BMW and CMW were determined in step 330. The six new coefficients, DM1, DM2, DM3, EM1, EM2 and EM3 can be calculated by substituting the pairs of values $(S_4, MW4)$ through $(S_9, MW9)$ into equation [1-21] and using matrix algebra operations to solve the six simultaneous equations. The resulting fully-determined equation [1-21] models molecular weight as a function of temperature, pressure, the speed of sound, the mole % concentration of carbon dioxide, and mole % concentration of nitrogen, measured at flowing pressure and temperature.

In Step 390, the speed of sound $S_{std}$ at standard pressure and temperature is calculated. The values of MW for the nine natural gas mixtures (three without diluents, and six with diluents) were determined in steps 305 and 340. Computer programming (such as SonicWare™ software) is used to calculate the speed of sound and the density for each of the nine reference mixtures, $G_1 \ldots G_9$ at standard pressure and temperature. The values of AMW, BMW and CMW are determined as in step 330, except that the newly-determined sound speed values are used for the natural gas mixtures without diluents, $G_1$, $G_2$ and $G_3$. Values for DM1, DM2, DM3, EM1, EM2 and EM3 can then be determined as in step 380 using the newly-determined sound speed values for the six natural gas mixtures with diluents, $G_4$, $G_5$, $G_6$, $G_7$, $G_8$, and $G_9$. Finally, the value of molecular weight determined in Step 380 is set equal to the model equation [1-21] using the coefficients calculated with the newly-determined sound speed values. The resulting equation can be solved iteratively for the standard sound speed at standard temperature and pressure for the gas mixture of unknown composition.

In Step 400, the mole % concentrations of carbon dioxide, $X_{CO2}$, and nitrogen, $X_{N2}$, are determined. These concentrations can be measured directly or obtained indirectly, as discussed above.

In Step 410, with the value of the standard sound speed now determined, together with the mole % concentrations of carbon dioxide, $X_{CO2}$, and nitrogen, $X_{N2}$, the inferential correlation equation [1-10] can be used to calculate the mass-based heating value, $H_m$, in units of Btu/lbm. The energy flow rate can be calculated by multiplying the value of the mass-based heating value $H_m$ by the natural gas mixture density derived in step 380, and the gas volumetric flow rate, as measured by a conventional flow meter. Since natural gas transmission companies prefer reporting the energy content of natural gas in units of Btu/standard cubic feet of volume, this quantity can be calculated as the product of the mass-based heating value $H_m$ multiplied by the "standard" density, $\rho_{std}$, which is in turn calculated using the inferential correlation equation [1-11].

Figure 4:
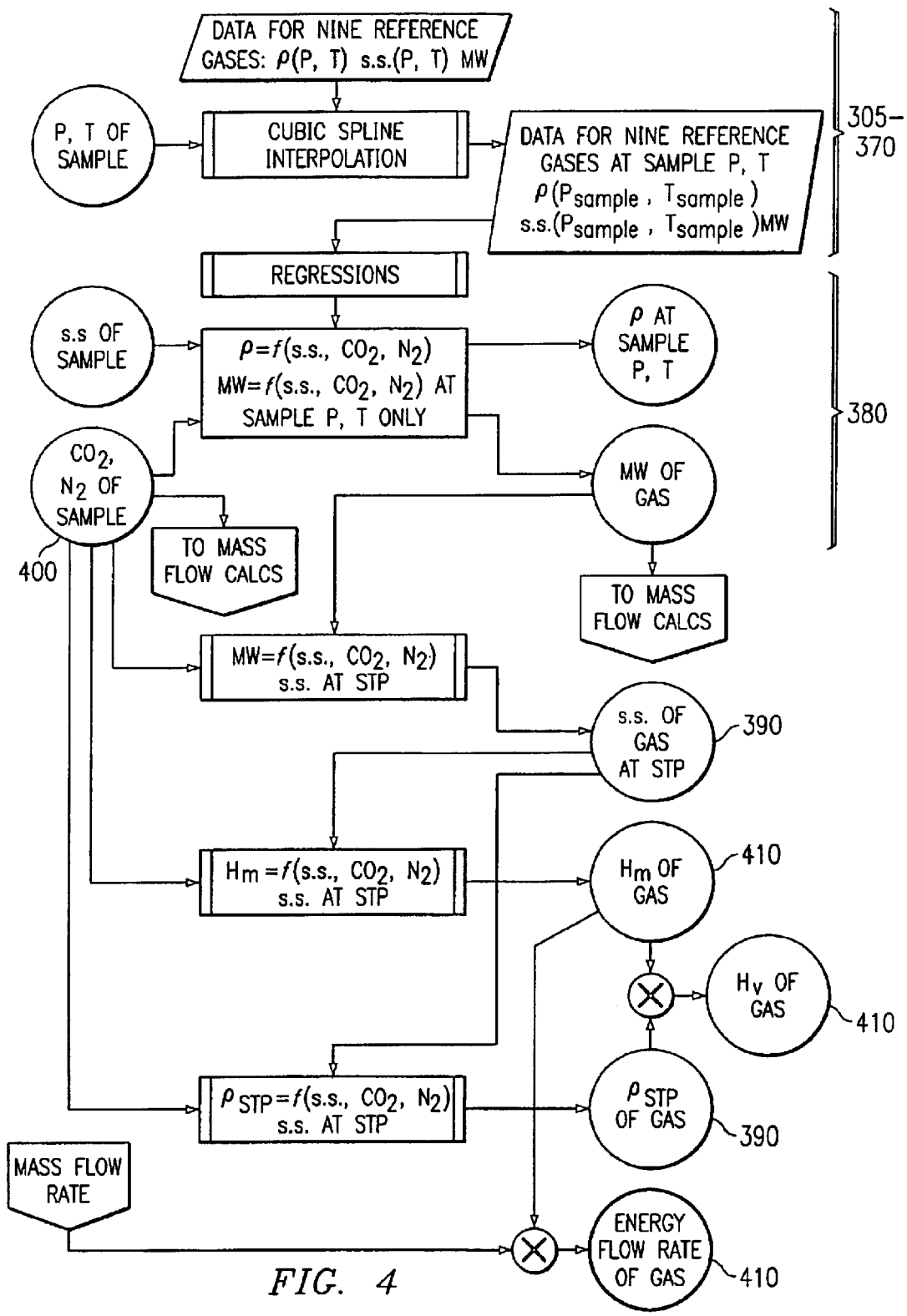
FIG. 4 further illustrates the method of FIG. 3.

FIG. 4 is an alternative illustration of the method of FIG. 3. FIG. 4 is a data flow type diagram. The emphasis is on the various calculations made after Steps 305–370, which involve obtaining the data for the nine references gases (three without diluents and six with diluents. As indicated, the density and molecular weight of the subject natural gas, which has an arbitrary temperature and pressure, can be estimated. Further energy measurement can then be calculated by using the estimated molecular weight and by calculating speed of sound at standard temperature and pressure. The calculation of the speed of sound at standard temperature and pressure is based on the same model equation as was used to find molecular weight and density, but now with speed of sound as the unknown value.

Other Embodiments

Many variations and modifications may be made to the disclosed embodiments of the invention without departing from the spirit and principles described herein. All such modifications and variations are intended to be included within the scope of the present invention, as defined by the following claims.

What is claimed is:

1. A computer product for determining the density of a subject gas mixture having both hydrocarbon and diluent components, and having known temperature, pressure, speed of sound, and diluent concentration values, the computer product having instructions for:

accessing a set of reference speed of sound and density values, derived from a set of reference gas mixtures, at least some of the gas mixtures containing diluents, at the known temperature and pressure;

modeling the density of a gas mixture as a function of its speed of sound, a number of coefficients, and its concentrations of diluent components, thereby obtaining a model equation;

using the reference speed of sound and reference density values to determine values for the coefficients;

substituting the coefficient values and the speed of sound and concentration values of the subject gas into the model equation; and solving the model equation to determine the density of the subject gas mixture.

2. The computer product of claim 1, wherein one of the diluent components is carbon dioxide.

3. The computer product of claim 1, wherein one of the diluent components is nitrogen.

4. The computer product of claim 1, wherein the density and speed of sound of the reference gas mixtures are determined by interpolating stored values of density and speed of sound over a range of temperature and pressure values.

5. The computer product of claim 1, wherein the density and speed of sound of the reference gas mixtures are calculated at the known pressure and temperature.

6. A computer product for determining the molecular weight of a subject gas mixture having both hydrocarbon and diluent components, and having known temperature, pressure, speed of sound, and diluent concentration values, the computer product having instructions for:

accessing a set of reference speed of sound and density values, derived from a set of reference gas mixtures, at least some of the gas mixtures containing diluents, at the known temperature and pressure;

modeling the molecular weight of a gas mixture as a function of its speed of sound, a number of coefficients, and its concentrations of diluent components, thereby obtaining a model equation;

using the reference speed of sound and reference density values to determine values for the coefficients;

substituting the coefficient values and the speed of sound and concentration values of the subject gas into the model equation; and solving the model equation to determine the molecular weight of the subject gas mixture.

7. The computer product of claim 6, wherein one of the diluent components is carbon dioxide.

8. The computer product of claim 6, wherein one of the diluent components is nitrogen.

9. The computer product of claim 6, wherein the density and speed of sound of the reference gas mixtures are determined by interpolating stored values of density and speed of sound over a range of temperature and pressure values.

10. The computer product of claim 6, wherein the density and speed of sound of the reference gas mixtures are determined by calculating those values at the known pressure and temperature.

11. A computer product for determining the heating value of a subject gas mixture having both hydrocarbon and diluent components, and having known temperature, pressure, speed of sound, and diluent concentration values, the computer product having instructions for:

accessing a set of reference speed of sound and density values, derived from a set of reference gas mixtures, at least some of the gas mixtures containing diluents, at the known temperature and pressure;

modeling the molecular weight of a gas mixture as a function of its speed of sound, a number of coefficients, and its concentrations of diluent components, thereby obtaining a model equation;

using the reference speed of sound and reference density values to determine values for the coefficients;

substituting the coefficient values and the speed of sound and concentration values of the subject gas into the model equation;

solving the model equation to determine the molecular weight of the subject gas mixture;

determining the speed of sound of the subject gas at standard temperature and pressure;

modeling a heating value of the subject gas as a function of its speed of sound at standard temperature and pressure, a number of coefficients, and its concentrations of diluent components, thereby obtaining a model equation; and solving the model equation to determine the heating value of the subject gas mixture.

12. The computer product of claim 11, wherein the heating value is a mass based heating value.

13. The computer product of claim 11, wherein one of the diluent components is carbon dioxide.

14. The computer product of claim 11, wherein one of the diluent components is nitrogen.

15. The computer product of claim 11, wherein the density and speed of sound of the reference gas mixtures are determined by interpolating stored values of density and speed of sound over a range of temperature and pressure values.

16. The computer product of claim 11, wherein the density and speed of sound of the reference gas mixtures are determined by calculating those values at the known pressure and temperature.

17. The computer product of claim 11, further comprising the steps of determining the mass flow rate of the subject gas mixture, and of using the mass flow rate and heating value to calculate the energy flow rate of the subject gas mixture.

* * * * *